US012101594B2

(12) United States Patent
Avagliano et al.

(10) Patent No.: US 12,101,594 B2
(45) Date of Patent: Sep. 24, 2024

(54) ACOUSTIC TRANSDUCERS, METHODS OF DESIGNING ACOUSTIC TRANSDUCERS, AND METHODS OF FORMING ACOUSTIC TRANSDUCERS

(71) Applicant: Baker Hughes Oilfield Operations LLC, Houston, TX (US)

(72) Inventors: Aaron Avagliano, Tomball, TX (US); Navin Sakthivel, Spring, TX (US); Chad Yates, Houston, TX (US); Brian Steven Wieneke, Spring, TX (US); Roger Steinsiek, Cypress, TX (US); Baskaran Ganesan, Acton, MA (US); Peter Leonard Wise, Ennis (IE); Benjamin Hoemske, Siegburg (DE); Sarah Elizabeth Austerman, Waltham, MA (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 0 days.

(21) Appl. No.: 17/196,780

(22) Filed: Mar. 9, 2021

(65) Prior Publication Data

US 2022/0295171 A1    Sep. 15, 2022

(51) Int. Cl.
*H04R 1/10* (2006.01)
*B22F 10/25* (2021.01)
(Continued)

(52) U.S. Cl.
CPC ......... *H04R 1/1058* (2013.01); *B22F 10/25* (2021.01); *B22F 10/28* (2021.01); *B22F 10/85* (2021.01); *H04R 1/02* (2013.01); *H04R 9/06* (2013.01)

(58) Field of Classification Search
CPC .......... H04R 1/1058; H04R 1/02; H04R 9/06; B29C 64/386; B29C 64/165; G06F 30/20;
(Continued)

(56) References Cited

U.S. PATENT DOCUMENTS 8,454,518 B2\*  6/2013  Saito .................... A61B 8/4444
                                                        600/407
9,525,393 B1\* 12/2016  Raihn ................... G06F 30/327
(Continued)

FOREIGN PATENT DOCUMENTS

KR       10-0951810 B1      4/2010

OTHER PUBLICATIONS

A Review of Acoustic Impedance Matching Techniques for Piezoelectric Sensors and Transducers, Sensors, Vivek T. Rathod, Sensors 20(14):4051, (Jul. 21, 2020).
(Continued)

*Primary Examiner* — Carolyn R Edwards
*Assistant Examiner* — Julie X Dang
(74) *Attorney, Agent, or Firm* — TraskBritt

(57) ABSTRACT

A method of designing and forming at least one element of an acoustic transducer. The method includes receiving one or more required operating parameters of the at least one element of the acoustic transducer for an application, iteratively modeling and simulating performance of one or more materials to utilize within the at least one element of the acoustic transducer, iteratively modeling and simulating performance of one or more structures to utilize within the at least one element of the acoustic transducer, identifying at least one material and at least one structure that exhibit predicted performance that at least achieves the one or more required operating parameters of the at least one element of the acoustic transducer for the application, outputting a design of the at least one element of the acoustic transducer,
(Continued)

and forming the at least one element of the acoustic transducer via one or more additive manufacturing processes.

19 Claims, 12 Drawing Sheets

(51) Int. Cl.
    *B22F 10/28* (2021.01)
    *B22F 10/85* (2021.01)
    *H04R 1/02* (2006.01)
    *H04R 9/06* (2006.01)

(58) Field of Classification Search
    CPC ...... G05B 19/4099; G05B 2219/49023; B33Y 10/00; B33Y 80/00; B33Y 50/00; B06B 1/067; G06N 20/20; G06N 20/00; B28B 1/001; B29L 2031/3406; B29K 2509/02; B29K 2995/0003; B29K 2063/00
    See application file for complete search history.

(56) References Cited

U.S. PATENT DOCUMENTS

| | | | |
|---|---|---|---|
| 2002/0156379 A1* | 10/2002 | Angelsen | H04R 17/00 600/459 |
| 2003/0200068 A1 | 10/2003 | Tanaka et al. | |
| 2006/0150380 A1* | 7/2006 | Ossmann | B06B 1/067 29/25.35 |
| 2007/0222339 A1* | 9/2007 | Lukacs | B06B 1/0622 310/334 |
| 2011/0255227 A1* | 10/2011 | Murakami | B32B 27/302 29/829 |
| 2013/0122261 A1* | 5/2013 | Barnes | B29D 11/00432 427/596 |
| 2015/0258574 A1 | 9/2015 | Lin et al. | |
| 2016/0040403 A1* | 2/2016 | Giesinger | B60R 15/00 137/15.01 |
| 2016/0050503 A1* | 2/2016 | Naether | H04R 25/60 264/308 |
| 2016/0151977 A1* | 6/2016 | Burd | B29C 64/386 700/98 |
| 2016/0310077 A1* | 10/2016 | Hunter | A61B 5/6862 |
| 2017/0289715 A1 | 10/2017 | Lan et al. | |
| 2018/0036964 A1* | 2/2018 | DehghanNiri | B29C 64/393 |
| 2020/0107816 A1* | 4/2020 | Lee | A61B 8/4455 |
| 2020/0268358 A1* | 8/2020 | Morita | B06B 1/0651 |
| 2021/0113187 A1* | 4/2021 | Morita | A61B 8/445 |
| 2021/0237122 A1* | 8/2021 | Hill | B06B 1/0681 |
| 2021/0328131 A1* | 10/2021 | Furuta | A61B 8/4444 |

OTHER PUBLICATIONS

Controlled-Source Analogous Circuits and SPICE Models for Piezoelectric Transducers, W. Marshall Leach, Jr., Ultrasonics, Ferroelectrics and Frequency Control, IEEE Transactions on, vol. 41, No. 1, pp. 60-66, 1994.

International Search Report and Written Opinion for International Application No. PCT/US22/070931, mailed Jun. 17, 2022, 7 pages.

\* cited by examiner

——— Using Standard Flat Impedance Matcher
--------- Using Additive 3D Printed Optimized Design Impedance

ACOUSTIC TRANSDUCERS, METHODS OF DESIGNING ACOUSTIC TRANSDUCERS, AND METHODS OF FORMING ACOUSTIC TRANSDUCERS

TECHNICAL FIELD

This disclosure relates generally to acoustic transducers. This disclosure further relates to methods of designing and forming acoustic transducers. This disclosure also relates to methods of forming one or more elements of acoustic transducers via additive manufacturing processes.

BACKGROUND

Acoustic transducers (e.g., piezoelectric transducers) are utilized in a wide variety of applications. For example, acoustic transducers are conventionally used in force microscopy, nano-positioning, micromechanical systems (MEMS), nanoelectromechanical systems (NEMS), energy harvesters, microphones, headphones, loudspeakers, acoustic emission sensors, vibration sensors, fluid characteristic sensors, inertial sensors, tactile sensors, power harvesting, ultrasound transducers, and guided wave sensors. Recently, use of acoustic transducers in various applications has surged due to their ability to produce real-time high resolution 3D images of a target load (e.g., fluid, biological tissue, etc.).

Efficiency of performance of acoustic transducers depends on the proper matching of electric and acoustic impedances, especially when considered during design stages. Furthermore, proper matching is limited by conventional design and manufacturing process.

BRIEF SUMMARY

One or more embodiments of the present disclosure include a method of designing at least one element of an acoustic transducer. The method may include receiving one or more required operating parameters of the at least one element of the acoustic transducer for an application, iteratively modeling and simulating performance of one or more materials to utilize within the at least one element of the acoustic transducer, iteratively modeling and simulating performance of one or more structures to utilize within the at least one element of the acoustic transducer, and identifying at least one material and at least one structure that exhibit predicted performance that at least substantially achieves the one or more required operating parameters of the at least one element of the acoustic transducer for the application.

Additional embodiments of the present disclosure include a method of forming a plurality of elements of an acoustic transducer. The method may include receiving a three-dimensional model design of the plurality of elements of the acoustic transducer, forming the plurality of elements of the acoustic transducer via one or more additive manufacturing processes, and forming at least one element of the plurality of elements of the acoustic transducer with one or more of a high temperature resin, polyetherimide, a nickel-chromium alloy, a stainless steel, nickel, titanium, silicon bronze, brass, aluminum, manganese, MONEL, or any alloys thereof.

Some embodiments of the present disclosure include a method of forming an acoustic transducer. The method may include receiving one or more required operating parameters of each of a piezoelectric ceramic crystal, matching layer, and a backing layer of the acoustic transducer for an application, iteratively modeling and simulating performance of one or more materials to utilize within the piezoelectric ceramic crystal, the matching layer, and the backing layer of the acoustic transducer, iteratively modeling and simulating performance of one or more structures to utilize within the piezoelectric ceramic crystal, the matching layer, and the backing layer of the acoustic transducer, identifying at least one material and at least one structure that exhibit predicted performance that at least substantially achieves the one or more required operating parameters of each of the piezoelectric ceramic crystal, the matching layer, and the backing layer of the acoustic transducer for the application, outputting a design of each of the piezoelectric ceramic crystal, the matching layer, and the backing layer of the acoustic transducer based at least partially on the identified at least one material and the identified at least one structure of each of the piezoelectric ceramic crystal, the matching layer, and the backing layer of the acoustic transducer, and forming each of the piezoelectric ceramic crystal, the matching layer, and the backing layer of the acoustic transducer via one or more additive manufacturing processes.

BRIEF DESCRIPTION OF THE DRAWINGS

For a detailed understanding of the present disclosure, reference should be made to the following detailed description, taken in conjunction with the accompanying drawings, in which like elements have generally been designated with like numerals, and wherein.

DETAILED DESCRIPTION

Figure 1A:
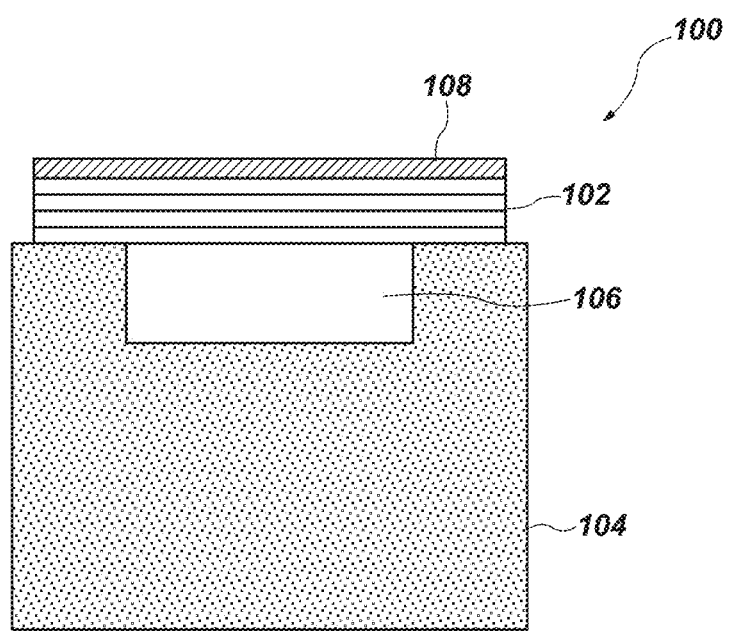
FIG. 1A is a schematic cross-sectional side view of an acoustic transducer according to one or more embodiments of the present disclosure.

The illustrations presented herein are not actual views of any particular acoustic transducer, additive manufacturing system, or any component of such, but are merely idealized representations, which are employed to describe the present invention.

As used herein, any relational term, such as "first," "second," "front," "back," etc., is used for clarity and convenience in understanding the disclosure and accompanying drawings, and does not connote or depend on any specific preference or order, except where the context clearly indicates otherwise.

As used herein, the terms "comprising," "including," "containing," "characterized by," and grammatical equivalents thereof are inclusive or open-ended terms that do not exclude additional, un-recited elements or method steps, but also include the more restrictive terms "consisting of," "consisting essentially of," and grammatical equivalents thereof.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

As used herein, the term "configured" refers to a size, shape, material composition, and arrangement of one or more of at least one structure and at least one apparatus facilitating operation of one or more of the structure and the apparatus in a predetermined way.

As used herein, the singular forms following "a," "an," and "the" are intended to include the plural forms as well, unless the context clearly indicates otherwise.

As used herein, the term "and/or" includes any and all combinations of one or more of the associated listed items.

As used herein, the term "substantially" in reference to a given parameter, property, or condition means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

As used herein, the term "about" used in reference to a given parameter is inclusive of the stated value and has the meaning dictated by the context (e.g., it includes the degree of error associated with measurement of the given parameter).

Some embodiments of the present disclosure include methods of designing and forming acoustic transducers. In particular, embodiments of the present disclosure include methods for forming application-specific tunable impedance matching layers, backing layers, and piezoelectric ceramic crystals of acoustic transducers. The design and formation of each application-specific acoustic transducer may be varied depending on conditions and characteristics of a target load and/or medium (e.g., fluid) to be sensed (e.g., a given application). Embodiments of the present disclosure addresses problems in customizing elements of an acoustic transducer in a case-by-case basis by utilizing additive manufacturing designs and processes to form elements having tunable (e.g., selectable) acoustic properties.

FIG. 1A shows an acoustic transducer 100 according to one or more embodiments of the disclosure. In some embodiments, the acoustic transducer 100 may include an additive manufactured acoustic transducer. For example, one or more elements of the acoustic transducer 100 may be formed via additive manufacturing process. In one or more embodiments, the acoustic transducer 100 may include an impedance matching layer 102, a backing layer 104 (also referred to as backing material and backing element), a piezoelectric ceramic crystal 106, and an acoustic lens 108.

In some embodiments, the backing material 104 may be disposed on a first side of the piezoelectric ceramic crystal 106 (e.g., a back side of or behind the piezoelectric ceramic crystal 106), and the impedance matching layer 102 may be disposed a second, opposite side of the piezoelectric ceramic crystal 106 (e.g., a front side or in front of the piezoelectric ceramic crystal 106). In operation, the piezoelectric ceramic crystal 106 may vibrate (i.e., generate an acoustic wave) in response to an applied voltage or may generate a voltage in response to an applied vibration (e.g., an acoustic wave (e.g., an ultrasonic wave)). The backing material 104 may prevent the piezoelectric ceramic crystal 106 from excessively vibrating. By reducing excessive vibration, the backing material 104 may cause the piezoelectric ceramic crystal 106 to generate acoustic waves with a shorter pulse length, which may improve resolution of ultimate output data (e.g., received acoustic waves that are converted to voltages) of the acoustic transducer 100. Additionally, when the backing material 104 has a high absorption, the backing material 104 may prevent spurious reflection from a back of the acoustic transducer. As a non-limiting example, an acoustic impedance of ≥6.0 MRayl may be used to optimize operation parameters (e.g., pulse-echo parameters) of the acoustic transducer 100.

The impedance matching layer 102 may enable acoustic waves to efficiently enter a medium (e.g., a fluid) being measured and/or sensed. For example, the impedance matching layer 102 may substantially match an impedance of the medium being tested and may at least substantially prevent the acoustic waves from reflecting off the medium being tested. Put another way, the impedance matching layer 102 may reduce reflection of the acoustic waves emitted by the piezoelectric ceramic crystal 106 by the medium being tested. In some embodiments, the acoustic lens 108 may focus the acoustic waves and may reduce or prevent spreading of the acoustic waves, which may ultimately improve resolution of output data of the acoustic transducer 100.

Referring still to FIG. 1A, as a non-limiting example, one or more quarter-wave impedance matching layers with acoustic impedance (ZMn) may be used to transform an impedance of an active piezoelectric ceramic crystal (ZA) to more closely match a medium (ZB) through which the acoustic waves may be propagated (e.g., a front propagating media). The energy transmission through a single quarter-wave matching layer is maximized when the acoustic impedance of the single quarter-wave matching layer is the geometric mean of the piezoelectric ceramic crystal (ZA) and the medium (ZB), as represented in the following:

$$Z_M = \sqrt{Z_A Z_B}$$

Additionally, designs of single and multiple matching layers may optimize pulse-echo performance parameters of an acoustic transducer. Optimizing pulse-echo performance parameters of an acoustic transducer for a single matching layer may be represented by the following:

$$Z_M = \sqrt{Z_A^{1/3} Z_B^{2/3}}$$

Optimizing pulse-echo performance parameters of an acoustic transducer for a double matching layer may be represented by the following:

$$Z_{M1} = \sqrt{Z_A^{4/7} Z_B^{3/7}}$$
$$Z_{M2} = \sqrt{Z_A^{1/7} Z_B^{6/7}} 1$$

Embodiments of the present disclosure include an acoustic transducer 100 having one or more elements (e.g., impedance matching layer 102, the backing layer 104, the piezoelectric ceramic crystal 106, and/or the acoustic lens 108) thereof being formed via additive manufacturing (e.g., 3D printing). As is described in greater detail below, forming one or more elements of the acoustic transducer 100 via additive manufacturing may improve impedance matching, enable selectable bandwidths, enable selectable sensitivity and resolution, improve energy transmission and reduce losses, control damping effects, etc.

As a non-limiting example, the acoustic transducer 100 and/or any element thereof can be formed via any suitable additive manufacturing processes known in the art. As a non-limiting example, in one or more embodiments, the acoustic transducer 100 and/or any element thereof may be formed via one or more additive manufacturing processes, such as, for example, binder jetting, stereolithography (SLA), sol-gel or liquid dispense methods, inkjet 3D printing, direct metal deposition, micro-plasma powder deposition, direct laser sintering, selective laser sintering, electron beam melting, electron beam freeform fabrication, fused deposition modeling, and other additive manufacturing processes. In some embodiments, each element of the acoustic transducer 100 may be formed via a same additive manufacturing process. In other embodiments, one or more elements of the acoustic transducer 100 may be formed via differing additive manufacturing processes. Furthermore, as is described in further detail below, in some embodiments, an entirety of the acoustic transducer 100 may be formed via a single additive manufacturing process and a single additive manufacturing system. In other embodiments, one or more elements of the acoustic transducer 100 may be for via a first additive manufacturing process and a first additive manufacturing system, and one or more elements of the acoustic transducer 100 may be for via a second additive manufacturing process and a second additive manufacturing system. Subsequently, the elements of the acoustic transducer 100 may be assembled.

Figure 1B:
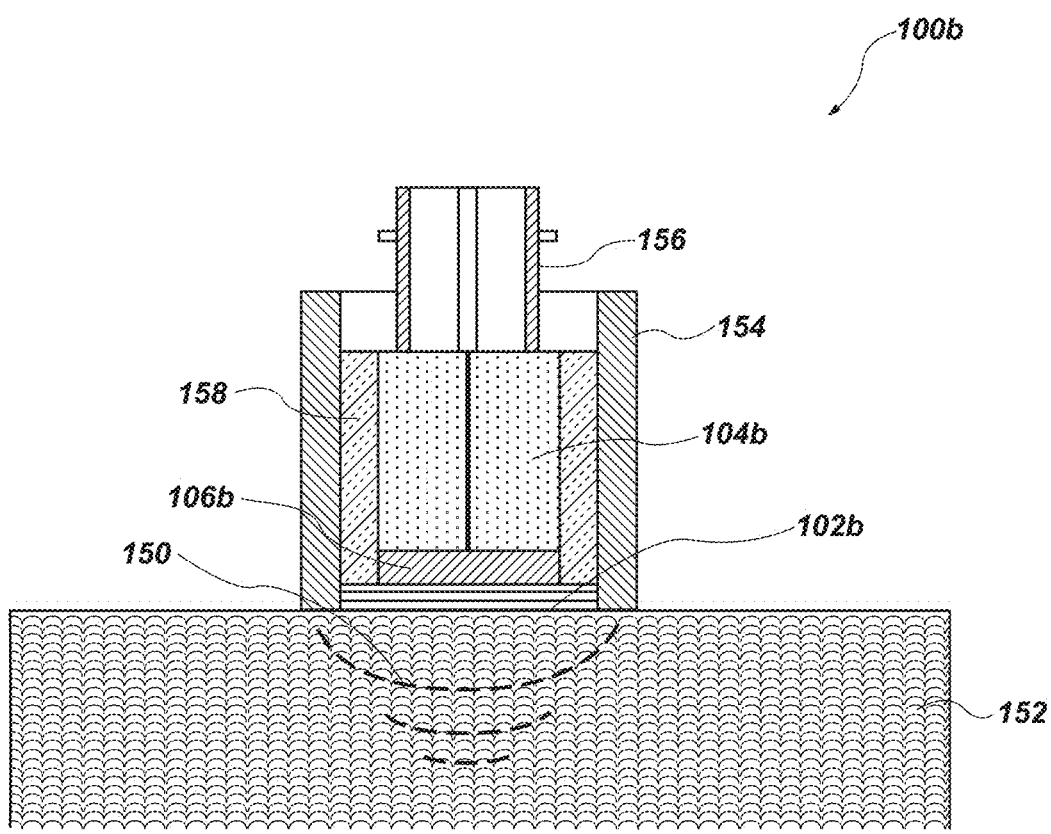
FIG. 1B is a schematic cross-sectional side view of another acoustic transducer according to one or more embodiments of the present disclosure.

FIG. 1B shows an acoustic transducer 100b according to one or more embodiments of the disclosure. Similar to the acoustic transducer 100 described above in regard to FIG. 1A, the acoustic transducer 100b may include an additive manufactured acoustic transducer. In one or more embodiments, the acoustic transducer 100b may include an impedance matching layer 102b, a backing layer 104b, a piezo-electric ceramic crystal 106b, an insulation material 158, a casing 154, and a connector 156.

In some embodiments, the backing material 104b may be disposed on a first side of the piezoelectric ceramic crystal 106b, and the impedance matching layer 102b may be disposed a second, opposite side of the piezoelectric ceramic crystal 106b. The insulation material 158 may at least partially surround the backing material 104b and the piezoelectric ceramic crystal 106b and may be disposed between the backing material 104b and the piezoelectric ceramic crystal 106b and the casing 154. The connector 156 may be coupled to the backing material 104b on a side opposite the impedance matching layer 102b.

In operation, the piezoelectric ceramic crystal 106b may vibrate and generate an acoustic wave 150 in response to an applied voltage or may generate a voltage in response to an applied vibration (e.g., an acoustic wave (e.g., an ultrasonic wave)). As discussed herein, the acoustic transducer 100b may be utilized to emit the acoustic wave 150 into a medium 152 (e.g., a wave propagating media).

Embodiments of the present disclosure include an acoustic transducer 100b having one or more elements (e.g., impedance matching layer 102b, the backing layer 104b, the piezoelectric ceramic crystal 106b) thereof being formed via additive manufacturing (e.g., 3D printing). As is described in greater detail below, forming one or more elements of the acoustic transducer 100b via additive manufacturing may improve impedance matching, enable selectable bandwidths, enable selectable sensitivity and resolution, improve energy transmission and reduce losses, control damping effects, etc.

Figure 2:
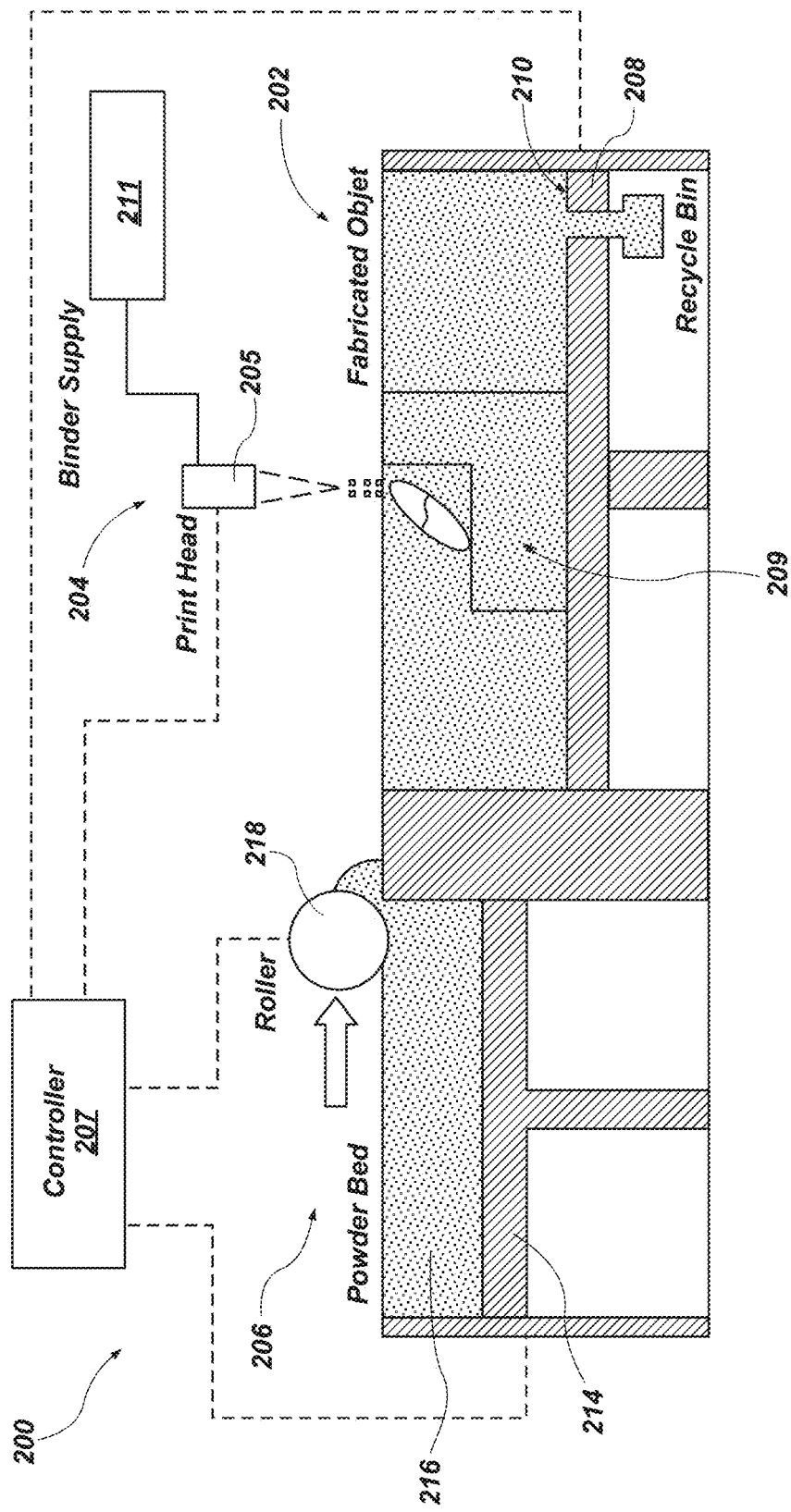
FIG. 2 is a partial cross-sectional view schematically illustrating an additive manufacturing system for forming acoustic transducer according to one or more embodiments of the present disclosure.

For clarity and by way of example and not limitation, a description of an example additive manufacturing method by which one or more elements of the acoustic transducers 100, 100b may be formed is provided below with reference to FIG. 2. FIG. 2 is a schematic view of an additive manufacturing system 200 according to one or more embodiments of the present disclosure. In some embodiments, the additive manufacturing system 200 includes a build assembly 202, a binder deposition system 204, a source material assembly 206, and a controller 207. Each of the build assembly 202, the binder deposition system 204, and the source material assembly 206 may be operably coupled to the controller 207. The build assembly 202 may include a build platform 208, a build plate 210 disposed on an upper surface of the build platform 208 and for supporting a part 209 (e.g., body) to be constructed, and one or more fasteners removably securing the build plate 210 to the build platform 208.

In some embodiments, the build platform 208 may include a piston, which translates in a vertical direction (e.g., a vertical Z axis) during part 209 formation. Furthermore, the build platform 208 may incrementally lower in a vertical direction during a part 209 printing process. For instance, the build platform 208 may include any conventional build platform known in the art.

The source material assembly 206 may include a material delivery platform 214, a source material 216, and a material applicator 218. In some embodiments, the material delivery platform 214 may include a piston, which translates in the vertical direction (e.g., the vertical Z axis), and the source material 216 may be disposed upon the piston. For instance, the material delivery platform 214 may translate upward in the vertical direction during a part printing process, and the material applicator 218 (e.g., a powder roller, a powder blade) may move source material 216 from on top of the material delivery platform 214 to the build assembly 202.

For example, the material applicator 218 (e.g., a roller, a blade) may skim powder source material 216 from on top of the top of the material delivery platform 214 and may spread a layer over the build platform 208. For instance, the source material assembly 206 may include any conventional source material assembly 206 known in the art.

The binder deposition system 204 may include a printing head 205 and a binder supply 211. The printing head 205 deposits (e.g., jets) a binding agent onto the powder according to a part's geometry (e.g., one or more elements of the acoustic transducer 100). The binder deposition system 204 may direct the printing head 205 in the X and Y directions via conventional methods. For example, the binder deposition system 204 may include any conventional binder deposition system 204 known in the art. Subsequently, another layer of the source material 216 may be spread over the binding agent and the previous layer, and the process of spreading layers and depositing binding agent according to the part's geometry may be repeated to form layers of the part and, ultimately, form the part (e.g., one or more elements of the acoustic transducer 100) itself.

The controller 207 may include a processor, a memory, a storage device, an I/O interface, and a communication interface, which may be communicatively coupled by way of a communication infrastructure. In one or more embodiments, the processor includes hardware for executing instructions, such as those making up a computer program. The memory may be used for storing data, metadata, and programs for execution by the processor(s). The storage device includes storage for storing data or instructions. The I/O interface allows a user to provide input to, receive output from, and otherwise transfer data to and receive data from the additive manufacturing system 200. The communication interface can include hardware, software, or both. In any event, the communication interface can provide one or more interfaces for communication (such as, for example, packet-based communication) between the additive manufacturing system 200 and one or more other computing devices or networks.

In operation, the controller 207 may slice a three-dimensional model into layers via a conventional process to create a two-dimensional image of each layer. Subsequently, the material applicator 218 may spread a thin layer of source material 216 (e.g., 0.1 mm thick layer of material) over the build plate 210 and the build platform 208. The binder deposition system 204 may deposit a binding agent on the layer of source material 216 to fuse or bond a first layer of material according to the two-dimensional image of the first layer. The build platform 208 then incrementally lowers (e.g., lowers by the same amount as the thickness of the layer of source material 216), and the process repeats until the entire (or at least a portion) of the three-dimensional model is created. For instance, the additive manufacturing system 200 may operate in a conventional manner.

Referring to FIGS. 1A, 1B, and 2 together, the additive manufacturing system 200 may include one or more additive manufacturing systems in addition to or instead of a binder jetting system. For instance, the additive manufacturing system 200 may include additive manufacturing systems for performing one or more of stereolithography (SLA), sol-gel or liquid dispense methods, inkjet 3D printing, direct metal deposition, micro-plasma powder deposition, direct laser sintering, selective laser sintering, electron beam melting, electron beam freeform fabrication, fused deposition modeling, or other additive manufacturing processes.

Figure 3:
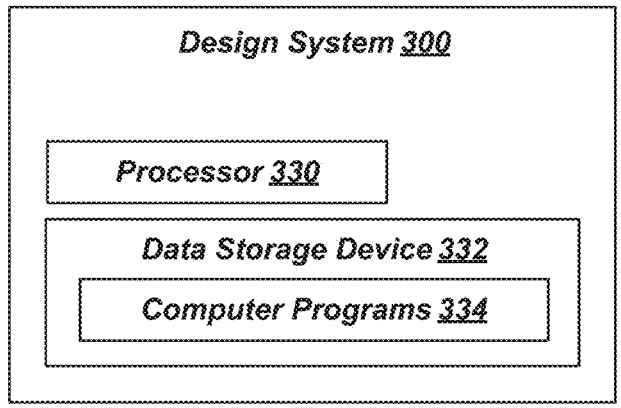
FIG. 3 shows a schematic view of a design system for designing acoustic transducers according to one or more embodiments of the present disclosure.

FIG. 3 shows a schematic view of a design system 300. The design system 300 may include a processor 330 and a data storage device 332 (or a computer-readable medium) for storing data, algorithms, and computer programs 334. The data storage device 332 may be any suitable device, including, but not limited to, a read-only memory (ROM), a random-access memory (RAM), a flash memory, a magnetic tape, a hard disk, and an optical disk. Additionally, the design system 300 may further include one or more devices for presenting output to an operator of the design system 300, including, but not limited to, a graphics engine, a display (e.g., a display screen), one or more output drivers (e.g., display drivers), one or more audio speakers, and one or more audio drivers. In certain embodiments, the design system 300 is configured to provide graphical data to a display for presentation to the operator. The graphical data may be representative of one or more graphical user interfaces and/or any other graphical content as may serve a particular implementation. As is described in greater detail in regard to FIGS. 4-8B, the design system 300 may generate predictive models of acoustic transducers having varying material compositions and geometries utilizing one or more machine learning techniques. Furthermore, based on the generated predictive models, the design system 300 may select material compositions and geometries to optimize performance (e.g., critical to quality ("CTQ") parameters) of the acoustic transducer for a given application.

Figure 4:
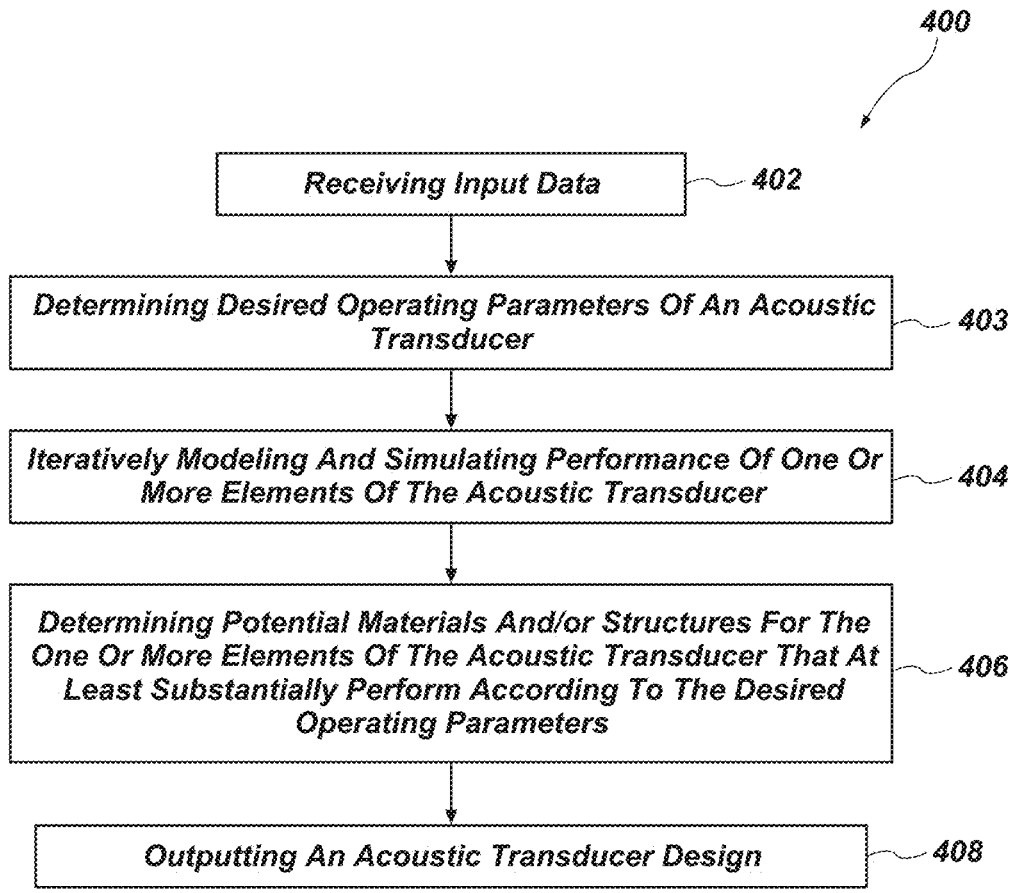
FIG. 4 shows a flowchart of a method of designing one or more elements of an acoustic transducer according to one or more embodiments of the present disclosure.

FIG. 4 shows a flowchart of a method 400 of designing one or more elements of an acoustic transducer (e.g., acoustic transducers 100, 100b). The acoustic transducers 100 and 100b may be referred to herein collectively as an "acoustic transducer 100" hereinafter. In some embodiments, the method 400 may include receiving input data, as shown in act 402 of FIG. 4. For example, the design system (e.g., design system 300) may receive the input data. In some embodiments, the input data may include historical data, sensor data, and/or application data (e.g., data regarding a given application within which an acoustic transducer is intended to be used). As used herein, the term "application" may refer to an environment (e.g., temperatures, pressures, environmental conditions, etc.) and a medium to be tested (e.g., a fluid) within which the acoustic transducer is intended to be used. In some embodiments, the historical data may include data regarding previously implemented acoustic transducers and performance data regarding those acoustic transducers and associated application data. The sensor data may include data from sensors disposed within environments within which the acoustic transducer is intended to be used. The application data may include environmental data (e.g., data regarding environmental conditions and size limitations) and medium data (e.g., data regarding the medium to be tested).

In some embodiments, the method 400 may further include determining desired (e.g., ideal) operating parameters (e.g., pulse-echo parameters) of an acoustic transducer 100 within a given application (e.g., the intended application of the acoustic transducer 100), as shown in act 403 of FIG. 4. For example, the design system 300 may determine optimized operating parameters for one or more elements of the acoustic transducer 100 based on the given application. Put another way, the design system 300 may define CTQs for the acoustic transducer 100 and the given application. For example, the design system 300 may define required frequencies of the acoustic transducers, desired footprint (e.g., size) of the acoustic transducers, signal strength requirements, bandwidth requirements, etc. As non-limiting examples, in regard to the piezoelectric ceramic crystal and the given application, the design system 300 may determine required or preferred operating parameters, such as optimized excitation levels, attenuation of back reflection, bandwidth, phase linearity, sensitivity, pulse-length, and pulse width for the given application. As another non-limiting example, in regard to the matching layer and the given application, the design system 300 may determine required or preferred (e.g., optimized) impedance of the impedance matching layer for the given application. As yet another non-limiting example, in regard to the backing material 104 and the given application, the design system 300 may determine required or preferred (e.g., optimized) attenuation or dampening levels of the backing material 104.

In some embodiments, the design system 300 may not determine the required or preferred operating parameters of the one or more elements of the acoustic transducer 100; rather, in such embodiments, the required or preferred operating parameters of the one or more elements of the acoustic transducer 100 may be input into the design system 300. In other words, the required or preferred operating parameters of the one or more elements of the acoustic transducer 100 for the given application may be included within the received input data. For instance, the design system 300 may receive required or preferred operating parameters of the one or more elements of the acoustic transducer 100 from an external source.

Responsive to receiving and/or determining the required or preferred operating parameters of the one or more elements of the acoustic transducer 100, the method 400 includes iteratively modeling and simulating performance (e.g., generating predictive performance models) of potential materials and structures (e.g., geometries) of one or more elements of the acoustic transducer 100 within the given application, as shown in act 404. As used herein, the term "performance" may refer to modeled and/or simulated operating parameters of the one or more elements of the acoustic transducer 100, such as the operating parameters described herein. For example, the method 400 includes iteratively modeling and simulating performance of the potential materials and structures of the one or more elements of the acoustic transducer 100 when applied to the given application. For instance, the method 400 may include varying one or more of aspects (e.g., a material composition, a density, a density gradient, a porosity, and/or an internal and/or external structure of the one or more elements) of the one or more elements and then modeling and simulating performance of the one or more elements. As a non-limiting example, modeling and simulating performance of the potential materials and structures of the one or more elements of the acoustic transducer 100 when applied to the given application may incrementally adjust one or more aspects of the one or more elements and model and simulate performance of each increment.

In some embodiments, the method 400 may include generating predictive models to tune material properties of the one or more elements of the acoustic transducer 100 for the given application. Additionally, the method 400 may include generating predictive models to tune the structure (e.g., geometry) of the one or more elements of the acoustic transducer 100 for the given application. Furthermore, the method 400 may include generating predictive models combining the tuned material properties and tuned structure (e.g., geometry) of the one or more elements of the acoustic transducer 100 for the given application. Moreover, as is described in further detail below, modeling and simulating performance of the potential materials and structures of the one or more elements of the acoustic transducer 100 when applied to the given application may include optimizing a design of an acoustic transducer 100 based on the predictive models described herein and to at least substantially meet the desired (e.g., ideal) operating parameters (e.g., CTQs) of the acoustic transducer 100.

In one or more embodiments, iteratively modeling and simulating potential materials may include iteratively modeling various different materials, various different material compositions, and various material gradients and material densities throughout the one or more elements of the acoustic transducer 100. In some embodiments, iteratively modeling and simulating potential materials may include iteratively modeling one or more of high temperature resins (e.g., high temperature SLA resins (e.g., photopolymer resin)), polyetherimide (e.g., an ULTEM resin), nickel-chromium alloys (e.g., INCONEL 718), stainless steel (e.g., Stainless steel 316 L), nickel, titanium, silicon bronze, brass, aluminum, manganese, MONEL, any alloy of the foregoing materials, or any other material. In regard to the piezoelectric ceramic crystal 106 of the acoustic transducer 100, iteratively modeling and simulating potential materials may include iteratively modeling various combinations of lead zirconium titanate (PZT) and polymer binders.

In one or more embodiments, iteratively modeling and simulating potential structures may include iteratively modeling various internal and external structures of the one or more elements of the acoustic transducer 100. For example, iteratively modeling and simulating potential structures may include modeling various internal and/or external lattice structures (e.g., honey comb structures, electric eel bionic structures, etc.) of the one or more elements of the acoustic transducer 100. Additionally, iteratively modeling and simulating potential structures may include modeling acoustic structures such as a conch structure, a trumpet horn structure, an ear drum cochlea shape, an elephant trunk shape, a golden ratio shape, etc. Moreover, iteratively modeling and simulating potential structures may include modeling various porosities and/or gradients of porosities within the one or more elements of the acoustic transducer 100. Furthermore, iteratively modeling and simulating potential structures may include modeling various densities and varying densities throughout the one or more elements of the acoustic transducer 100. For example, in regard to the matching layer ###, iteratively modeling and simulating potential structures may include modeling varying densities from layer to layer of the matching layer 102.

In some embodiments, iteratively modeling and simulating potential materials and structures of one or more elements of the acoustic transducer 100 may include utilizing one or more machine learning techniques and/or deep learning techniques to iteratively model and simulate performance of potential materials and structures of one or more elements of the acoustic transducer 100. For example, the design system 300 may utilize one or more machine learning techniques to iteratively model and simulate performance of the potential materials and structures of one or more elements of the acoustic transducer 100. In some embodiments, the machine learning and/or deep learning techniques may include one or more of regression models (e.g., a set of statistical processes for estimating the relationships among variables), classification models, and/or phenomena models. Additionally, the machine-learning techniques and/or deep learning techniques may include a quadratic regression analysis, a logistic regression analysis, a support vector machine, a Gaussian process regression, ensemble models, or any other regression analysis. Furthermore, in yet further embodiments, the machine-learning techniques and/or deep learning techniques may include decision tree learning, regression trees, boosted trees, gradient boosted tree, multilayer perceptron, one-vs-rest, Naive Bayes, k-nearest neighbor, association rule learning, a neural network, deep learning, pattern recognition, or any other type of machine-learning.

In some embodiments, the design system 300 may utilize historical data, feedback data, and/or known physics models, acoustics models, and/or mechanics models to train the machine-learning models to match material compositions, external structures, and/or internal structures with performance (e.g., operating parameters) of an acoustic transducer 100. In other words, via the machine learning model techniques, the design system 300 may learn correlations between input data (e.g., material compositions, external structures, and/or internal structures of the one or more elements of the acoustic transducer 100, data regarding the given application, etc.) and performance (e.g., operating parameters of the one or more elements). Put another way, the design system 300 may learn the relationship between the input data and the performance of the modeled/simulated acoustic transducer 100. For example, as will be understood in the art, for a given set of input values (e.g., given application and materials and structure of the one or more elements of the acoustic transducer 100), the design system 300 is expected to produce the consistent and accurate output values (i.e., performance data). In particular, the machine learning models may be trained via supervised learning, as is known in the art. After a sufficient number of iterations, the machine learning models become trained machine-learning models. In some embodiments, the machine learning models may also be trained on historical data from previously designed and implemented acoustic transducers.

Figure 9:
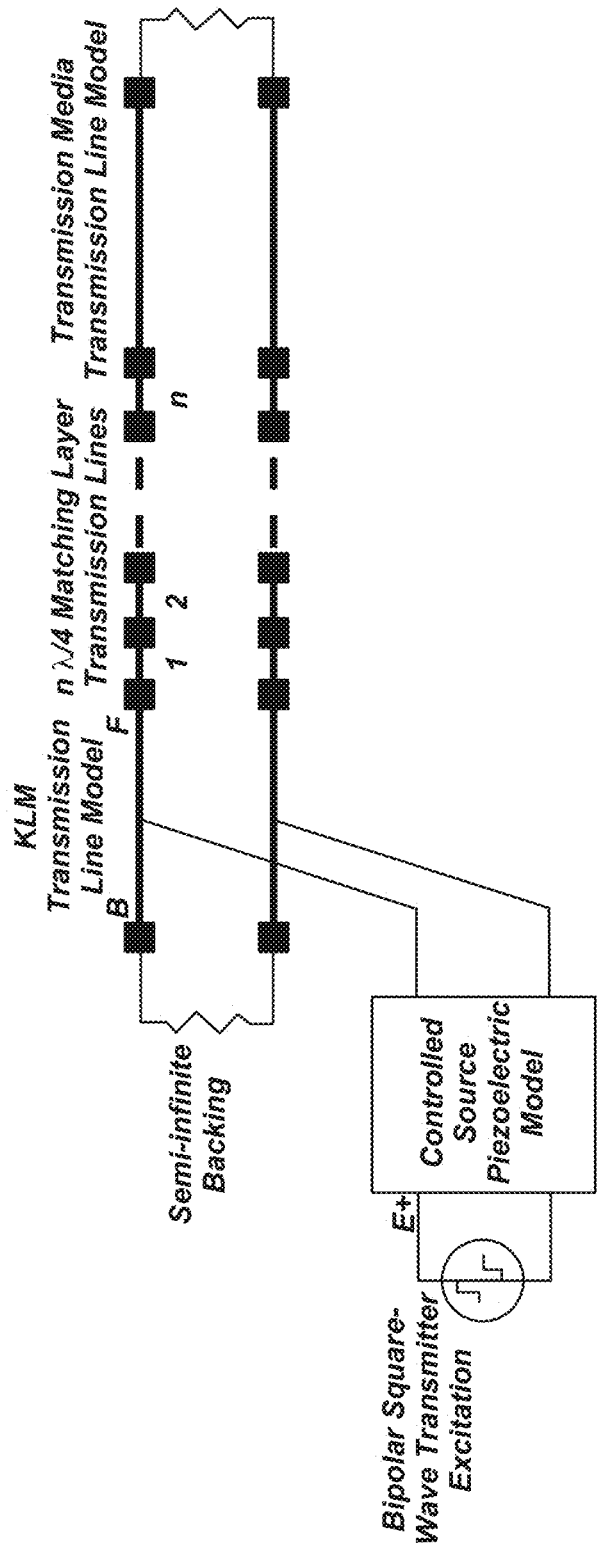
FIG. 9 shows an example one dimensional line model of at least a piezoelectric ceramic crystal according to one or more embodiments of the present disclosure.

Referring still to act 404 of FIG. 4, in some embodiments, each of the backing element 104, the matching layer 102, the piezoelectric ceramic crystal 106, and the medium 152 to be measured may be modeled using a one-dimensional transmission line model. FIG. 9 shows an example one dimensional line model of at least a piezoelectric ceramic crystal 106 according to one or more embodiments of the present disclosure. Referring to FIGS. 4 and 9 together, in one or more of the elements of the acoustic transducer 100 may be modeled according to any of the manners described in, for example, *Controlled-Source Analogous Circuits and SPICE Models for Piezoelectric Transducers*, W. Marshall Leach, Jr., Ultrasonics, Ferroelectrics and Frequency Control, IEEE Transactions on, vol. 41, no. 1, pp. 60-66,1994, the disclosure of which is incorporated in its entirety by reference herein.

Additionally, each of the backing element 104, the matching layer 102, the piezoelectric ceramic crystal 106, and the medium 152 to be measured may be modeled in one or more two-dimensional models and/or three-dimensional models.

The method 400 may further include determining (e.g., identifying) materials and/or structures that at least substantially perform according to the desired (e.g., ideal) operating parameters for the given application (e.g., achieve or meet the CTQs), as shown in act 406 of FIG. 4. For example, based at least partially on iteratively modeled and simulated performances of the materials and structures of the one or more elements of the acoustic transducer 100, the design system 300 may identify materials and/or structures that result in performance (e.g., performance of the one or more elements of the acoustic transducer 100) within the given application that at least substantially matches the desired operating parameters described above in regard to act 402 of FIG. 4. As a non-limiting example, in regard to the piezoelectric ceramic crystal 106, the design system 300 may identify materials and/or structures that at least substantially yield the optimized excitation levels, attenuation of back reflection, bandwidth, and pulse width for the given application. For example, in regard to the piezoelectric ceramic crystal 106, the design system 300 may identify materials and/or structures that yield desired elastic moduli, porosities, chemical compositions, crystal lattices, residual stresses, and/or electric polings, which determine piezo-electric properties of the piezoelectric ceramic crystal 106. As another non-limiting example, in regard to the matching layer 102, the design system 300 may identify materials and/or structures that at least substantially yield the optimized impedance of the impedance matching layer 102 for the given application (e.g., match impedance between a target load and the piezoelectric ceramic crystal 106). Furthermore, in regard to the matching layer 102, the design system 300 may identify materials and/or structures that at least substantially optimize transmission of pressure waves. As yet another non-limiting example, in regard to the backing material 104, the design system 300 may identify materials and/or structures that at least substantially yield the optimized attenuation or dampening levels of the backing material 104.

In some embodiments, determining (e.g., identifying) materials and/or structures that at least substantially perform according to the desired (e.g., ideal) operating parameters for the given application may include identifying materials and/or structures at best approach the desired (e.g., ideal) operating parameters. For example, in some instances, the exact desired (e.g., ideal) operating parameters may not be achievable via simulated materials and/or structures, and in such case, a best option may be identified.

Responsive to identifying materials and/or structures that at least substantially perform according to the desired (e.g., ideal) operating parameters for the given application, the method 400 may include outputting an acoustic transducer 100 design, as shown in act 408 as shown in FIG. 4. For example, the design system 300 may output (e.g., generate) a data package indicating a material composition and/or structure of one or more elements of the acoustic transducer 100. In some embodiments, the acoustic transducer 100 design may include a three-dimensional model of the acoustic transducer 100 that can be sliced into layers and utilized by one or more additive manufacturing systems. For instance, as is be described in further detail below, in some embodiments, the acoustic transducer 100 design may be output (e.g., transmitted) to one or more additive manufacturing systems (e.g., additive manufacturing system 200) for fabrication.

Figure 5A:
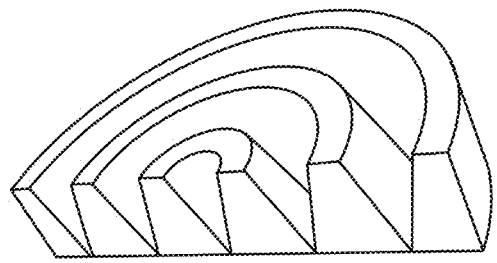
FIGS. 5A-5C depict example designs of a matching layer of an acoustic transducer generated via one or more of embodiments of the present disclosure.
Figure 5B:
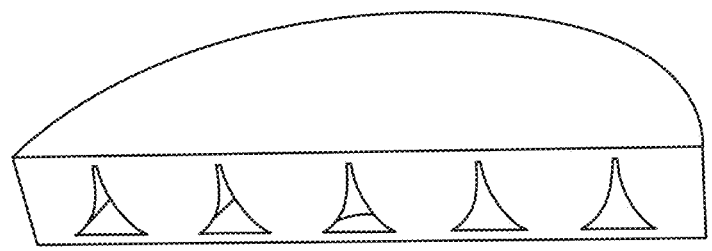
Figure 5C:
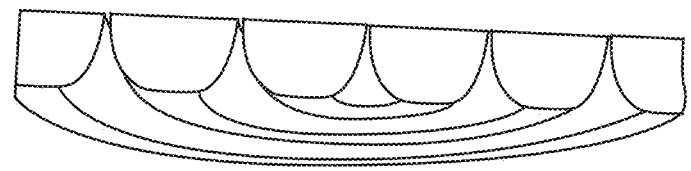

FIGS. 5A-5C depict example designs of matching layer 502a, 502b, 502c output via one or more of methods described herein (e.g., method 400). As shown in FIGS. 5A-5C, designing elements of an acoustic transducer 100 via the methods described herein may enable and result in elements having more complex geometries in comparison to conventional elements of the acoustic transducers in order to achieve the desired operating parameters. Furthermore, as is described in further detail below, because the designed elements of the acoustic transducer 100 are formed via additive manufacturing process, the complex geometries are able to be manufactured.

Figure 6:
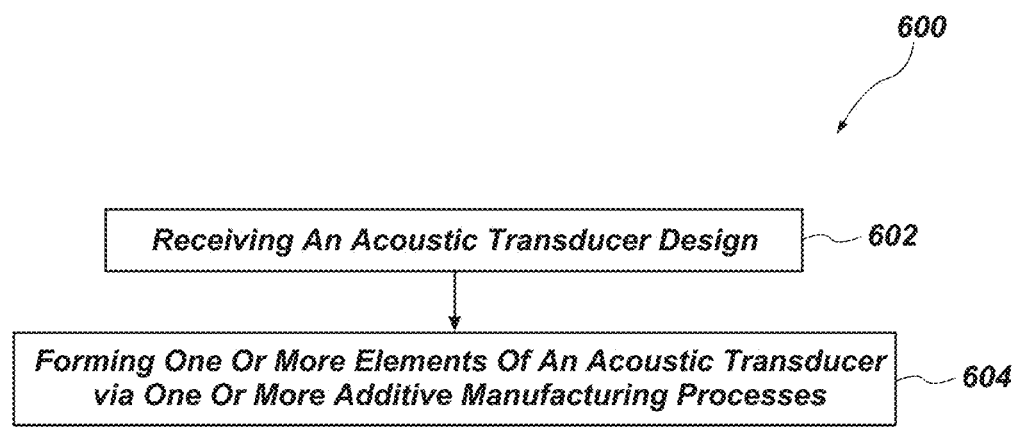
FIG. 6 shows a flowchart of a method of forming an acoustic transducer according to one or more embodiments of the disclosure.

FIG. 6 shows a flowchart of a method 600 of forming an acoustic transducer 100 according to one or more embodiments of the disclosure. In some embodiments, the method 600 may include forming one or more elements of the acoustic transducer 100 via one or more additive manufacturing processes. In one or more embodiments, the method 400 may include receiving an acoustic transducer design, as shown in act 602 of FIG. 6. For example, an additive manufacturing systems may receive the acoustic transducer design from the design system 300.

Responsive to receiving the acoustic transducer design, the method 600 may include forming one or more elements of the acoustic transducer 100 via one or more additive manufacturing processes, as shown in act 604 of FIG. 6. For example, one or more additive manufacturing systems (e.g., additive manufacturing system 200) may form one or more elements of the acoustic transducer 100 via one of binder jetting, SLA, sol-gel of liquid dispensing, inkjet 3D printing, direct metal deposition, micro-plasma powder deposition, direct laser sintering, selective laser sintering, electron beam melting, fused deposition modeling, or electron beam freeform fabrication.

In some embodiments, the method 600 may include forming each element (e.g., the impedance matching layer, the backing layer, and the piezoelectric ceramic crystal) of the acoustic transducer 100 via one or more additive manufacturing processes. In other embodiments, the method 600 may include forming one or more elements but not all elements via one or more additive manufacturing processes. In one or more embodiments, the method 600 may include forming a first element of the acoustic transducer 100 via a first additive manufacturing process and a second element of the acoustic transducer 100 via a second additive manufacturing process. In additional embodiments, the method 600 may include forming each element of the acoustic transducer 100 via a same additive manufacturing process.

In one or more embodiments, the method 600 may include forming each element (e.g., the impedance matching layer 102, the backing layer 104, and the piezoelectric ceramic crystal 106) of the acoustic transducer 100 in a single additive manufacturing process. For example, an entirety of the acoustic transducer 100 (e.g., the impedance matching layer 102, the backing layer 104, and the piezoelectric ceramic crystal 106 of the acoustic transducer 100) may be printed simultaneously, substantially simultaneous, or consecutively during a single additive manufacturing process. In other embodiments, the method 600 may include forming elements of the acoustic transducer 100 via multiple additive manufacturing processes. For example, at least one first element of the acoustic transducer 100 may be formed during a first additive manufacturing process and at least one second element of the acoustic transducer 100 may be formed during a second additive manufacturing process. Subsequently, the at least one first element and the at least one second element may be assembled together to form the acoustic transducer 100.

Referring still to FIG. 6, in some embodiments, the method 600 may include forming one or more elements of the acoustic transducer 100 with one or more of high temperature resins (e.g., high temperature SLA resins (e.g., photopolymer resin)), polyetherimide (e.g., an UL IEM resin), nickel-chromium alloys (e.g., INCONEL 718), stainless steel (e.g., Stainless steel 316 L), nickel, titanium, silicon bronze, brass, aluminum, manganese, MONEL, or any alloys thereof. Additionally, the method 400 may include forming the piezoelectric ceramic crystal 106 with a combination of lead Zirconium Titanate (PZT) and a polymer binder. In some embodiments, the polymer binder may include an ultra-violet curing polymer or resin (e.g., epoxy terminated silicon, odonium salt, photosensitizer, and silica). In additional embodiments, the polymer binder may include two-part room temperature/thermal cure epoxy resins. In yet further embodiments, the piezoelectric ceramic crystal 106 may include one or more of $PbNb_2O_6$ (modified lead metaniobates), $Bi_4Ti_3O_{12}$ (used in conjunction with PZT in sol-gel processes), or $LiNbO_3$ single crystals. In addition, the piezoelectric ceramic crystal 106 may include acceptor or donor dopants to adjust (e.g., improve) base performance of the piezoelectric ceramic crystal 106.

As will be recognized by one of ordinary skill in the art, one or more of the above listed materials is not a conventional material utilized within elements of conventional acoustic transducers. However, modeling and simulations performed by the inventors have pointed to configurations and designs utilizing one or more unconventional materials in forming one or more elements of the acoustic transducer 100. For example, modeling and simulations have pointed to using nickel-chromium alloys for one or more elements of the acoustic transducer 100. In view of the foregoing, unconventional materials were found to be effective in operating at least substantially according to desired operating parameters of the acoustic transducer 100. Therefore, the methods of designing acoustic transducers described herein have yielded unexpected results by generating designs that include unconventional materials. Furthermore, the methods forming acoustic transducers described herein have yielded unexpected results by utilizing unconventional materials. Moreover, the acoustic transducers formed via the methods described herein yield unexpected results by effectively achieve the desired operating parameters while utilizing unconventional materials.

Some embodiments of the disclosure include methods combining methods 400 and 600. For instance, methods of the present disclosure may include method 400 followed by method 600.

Referring to FIGS. 1-6 together, designing one or more elements of the acoustic transducer 100 via iterative modeling and simulations and forming the one or more elements via additive manufacturing may be advantageous over conventional methods of designing and forming acoustic transducers and may provide acoustic transducers that are advantageous comparative to conventional acoustic transducers. For example, the methods described herein may enable properties of a piezoelectric ceramic crystal (e.g., piezoelectric ceramic crystal 106) to be selected and may produce piezoelectric ceramic crystals having the selected properties. For instance, the methods described herein may enable a piezo-electric constant, an electromechanical coupling factor, and a dielectric constant of the piezoelectric ceramic crystal 106 to be selected. Therefore, the methods described herein provide methods of tuning (e.g., selecting) operating parameters of a piezoelectric ceramic crystal 106 for a given application, such as excitation levels, attenuation of back reflection, bandwidth, and pulse width.

Additionally, the methods described herein may improve impedance matching in comparison to conventional impedance matching layer. For example, as mentioned above, because the matching layer 102 of the acoustic transducer 100 are formed via additive manufacturing processes, the matching layer 102 may be formed having more complex structures (e.g., geometrical features) in comparison to conventional matching layer, which may enable the matching layer 102 to more closely match an impedance of the target load (e.g., medium to be measured) and more efficiently transmit waves (e.g., pressure waves) in comparison to conventional matching layer.

Furthermore, because the backing layer 104 of the acoustic transducer 100 may be formed via additive manufacturing processes, the backing layer 104 may include more complex structures in comparison to conventional backing layers. For example, in some embodiments, the structure of the backing layer 104 may more closely approach natural designs such as coral reef. Having a more complex structures may enable an overall thickness of the backing layer 104 to be reduced relative to conventional backing layers. For example, relative to conventional backing layers, the backing layers 104 formed via the methods described herein may reduce a thickness of the backing layer 104 by at least 20%, at least 30%, or at least 50%.

Moreover, the embodiments described herein provide methods for selecting bandwidths over which acoustic transducers operate based on a target load and/or given application. Additionally, the embodiments described herein provide methods for selecting sensitivity and resolutions acoustic transducers may exhibit. Furthermore, the embodiments described herein provide methods for forming acoustic transducers exhibiting improved energy transmission relative to conventional acoustic transducers. Also, the embodiments described herein provide methods for forming acoustic transducers exhibiting selected (e.g., controlled) damping for a target load and/or given application. For example, the embodiments described herein provide methods for designing and forming acoustic transducers on a case-by-case basis.

Also, the embodiments described herein provide relatively low cost options for application specific (e.g., tunable) acoustic transducers. Furthermore, the embodiments described herein reduce design and manufacturing time relative to conventional methods for forming acoustic transducers. Additionally, the embodiments described herein may optimize material densities, infill packing moduli, chemical compositions, speeds at which sound passes through materials, dielectric constants, piezo-electric constants, and electromechanical coupling factor of acoustic transducers for a given application.

Figure 7A:
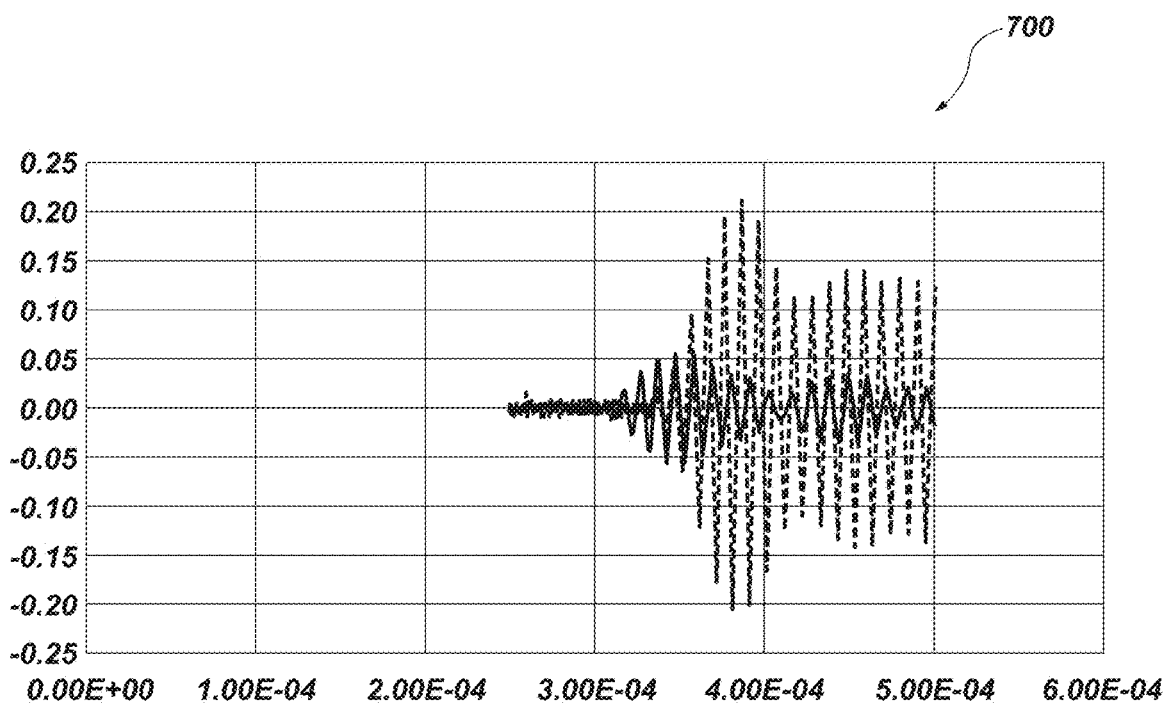
FIGS. 7A and 7B show graphs depicting actual testing of a signal strength and a predicted signal strength of a matching layer of an acoustic transducer designed and formed via the methods described herein relative to a conventional flat matching layer.
Figure 7B:
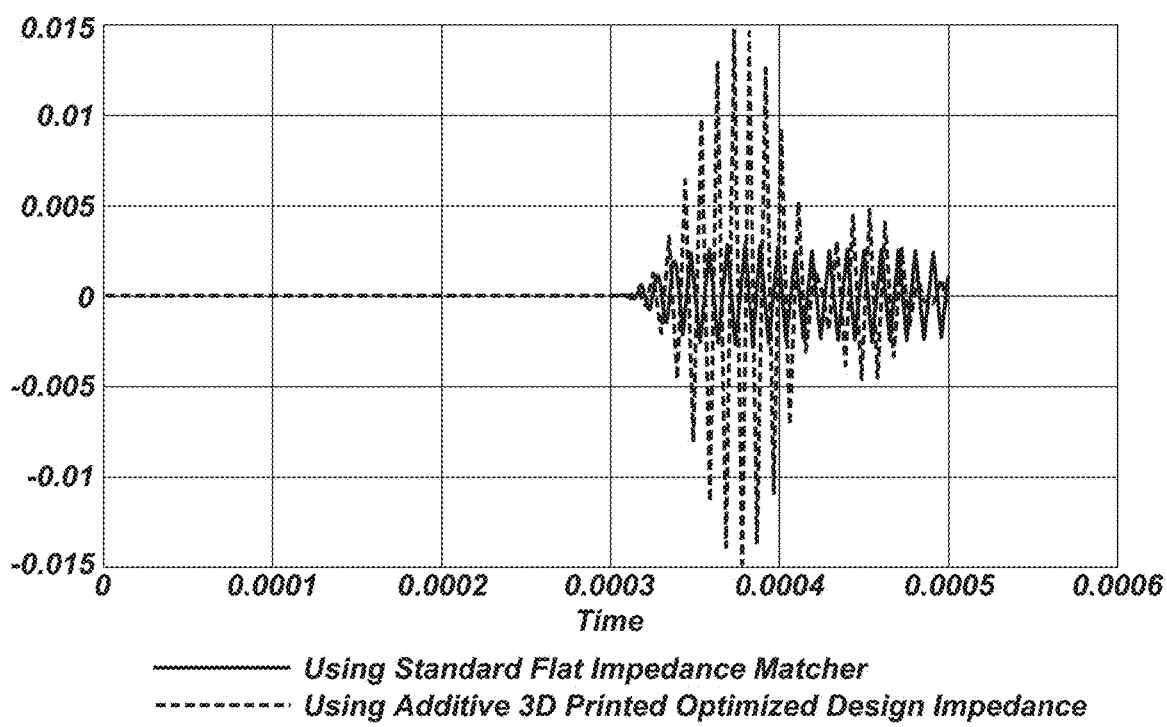

FIGS. 7A and 7B show graphs 700 and 702 depicting actual testing of a signal strength and a predicted signal strength of matching layer of an acoustic transducer 100 designed and formed via the methods described herein relative to conventional flat matching layer. As shown in FIGS. 7A and 7B, both that actual strength depicted by the acoustic transducer 100 and the predicted signal strength of the matching layer of the acoustic transducer 100 formed via the methods described herein were consistently about four times (4×) or about twelve dB higher than the conventional flat matching layer.

Figure 8A:
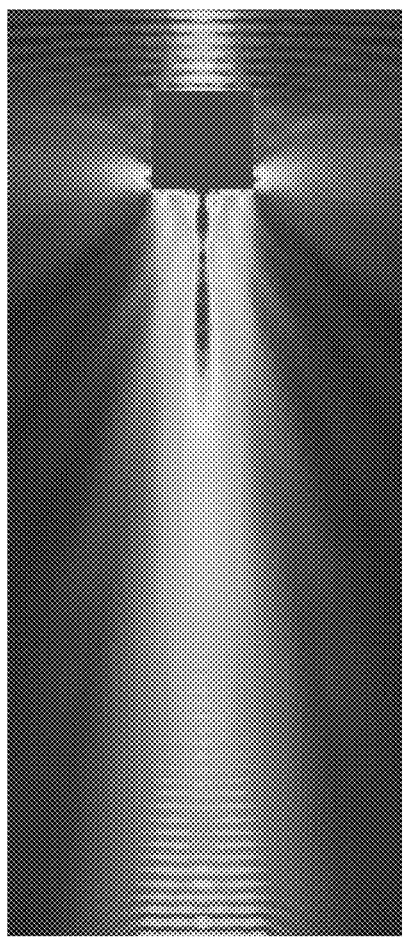
FIGS. 8A and 8B show depictions of signal transmission energy comparisons of a conventional acoustic transducer and an acoustic transducer formed via the methods described herein, respectively.
Figure 8B:
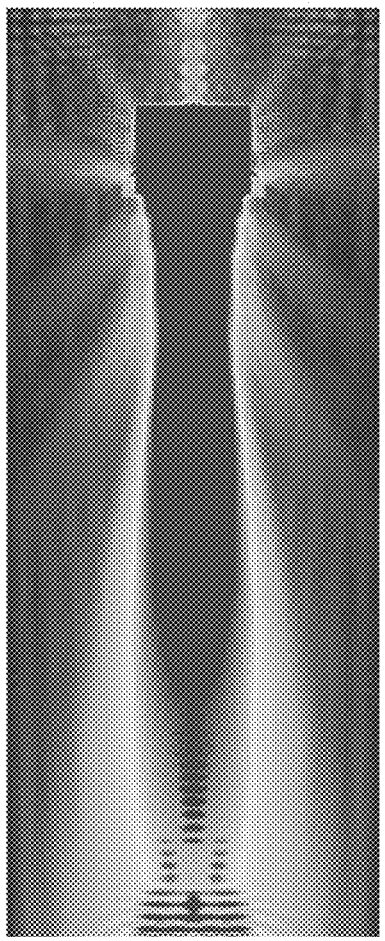

FIGS. 8A and 8B show depictions of signal transmission energy comparisons of a conventional acoustic transducer and an acoustic transducer 100 formed via the methods described herein.

Figure 10:
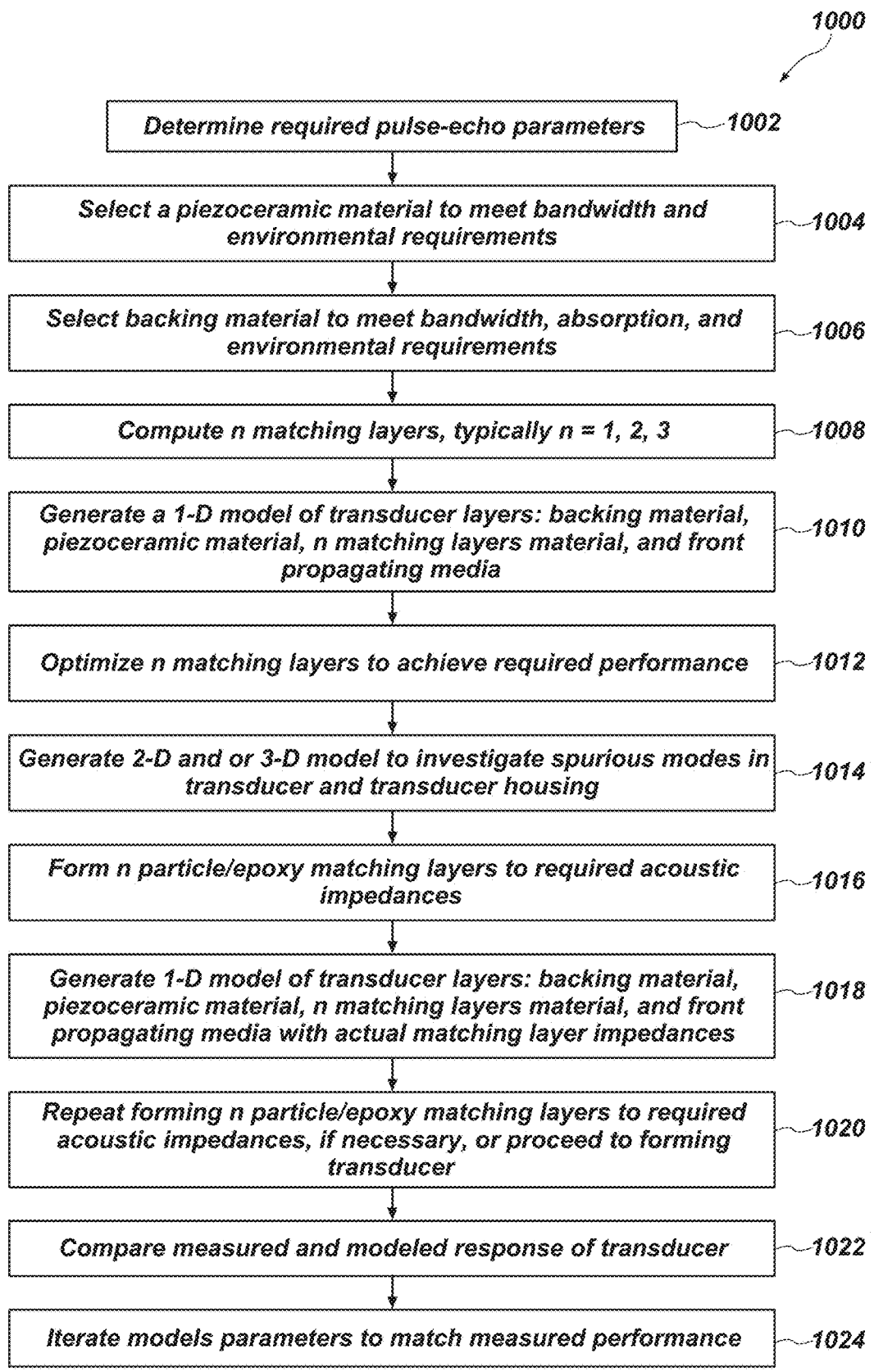
FIG. 10 shows an example flowchart of a method of designing and forming matching layer of an acoustic transducer according to one or more additional embodiments of the present disclosure.

FIG. 10 shows an example flowchart of a method 1000 of designing and forming matching layer of an acoustic transducer (e.g., acoustic transducers 100, 100b) according to one or more additional embodiments of the present disclosure. In some embodiments, the method 1000 may include determining required pulse-echo parameters, as shown in act 1002 of FIG. 10. Determining the required pulse-echo parameters (e.g., sensitivity, bandwidth, pulse-length, phase linearity, etc.) may include any of the actions described above in regard to acts 402 and 403 of FIG. 4.

The method 1000 may further include selecting a piezoelectric ceramic material to meet required bandwidth and environmental requirements of a given application, as shown in act 1004 of FIG. 10. For example, selecting a piezoelectric ceramic material to meet the required pulse-echo parameters may include any of the actions described above in regard to acts 404-408 of FIG. 4.

The method 1000 may also include selecting a backing material to meet bandwidth, absorption, and environmental requirements for the given application, as shown in act 1006 of FIG. 10. For instance, selecting a backing material to meet bandwidth, absorption, and environmental requirements may include any of the actions described above in regard to acts 404-408 of FIG. 4.

Additionally, the method 1000 may include computing a number (n) of matching layers for the given application, as shown in act 1008 of FIG. 10. For example, the number of matching layers may be determined via any conventional method.

The method 1000 may include generating a one-dimensional model of the acoustic transducers including the backing material, the piezoelectric ceramic material, the matching layers, and the medium (e.g., propagating media), as shown in act 1010 of FIG. 10. For example, generating a one-dimensional model may include generating a one-dimensional model via any of the manners described above in regard to FIGS. 4 and 9.

Based at least partially on the generated one-dimensional model, the method 1000 may include optimizing a number of matching layers to achieve the required pulse-echo parameters, as shown in act 1012 of FIG. 10. For example, the number of matching layers, material of matching layers, and structure of material layers may be optimized via any of the manners described above in regard to FIG. 4.

The method 1000 may further include generating two-dimensional and/or three-dimensional models of one or more elements of the acoustic transducer to predict and model spurious modes of the acoustic transducer and/or an acoustic transducer housing, as shown in act 1014 of FIG. 10. For example, the two-dimensional models and the three-dimensional models may be generated and analyzed via any of the manners described above in regard to FIG. 4.

Additionally, the method 1000 may include forming the matching layers according to the determined required acoustic impedances, as shown in act 1016 of FIG. 10. For instance, the method 1000 may include forming the matching layers via any of the manners described above in regard to FIGS. 2 and 6.

Furthermore, the method 1000 may include generating a one-dimensional model of the acoustic transducers including the backing material, the piezoelectric ceramic material, the matching layers, and the medium (e.g., propagating media) with actual matching layer impedances, as shown in act 1018 of FIG. 10. For instance, the one-dimensional model may be generated via any of the manners described above in regard to FIGS. 4 and 9.

Forming the matching layers may be repeated if necessary, or the method 1000 may proceed to forming the acoustic transducer as shown in act 1020 of FIG. 10. For instance, the acoustic transducer may be formed via any of the manners described above in regard to FIGS. 2 and 6.

Figure 11:
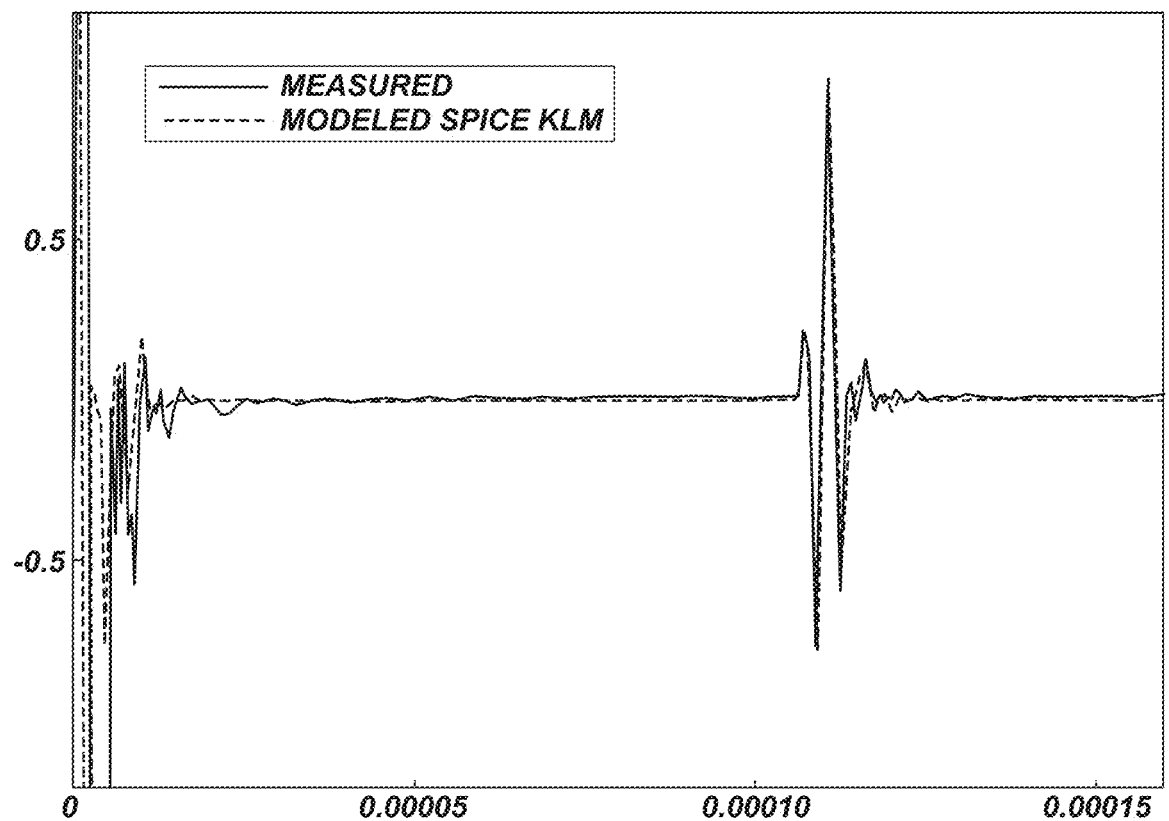
FIG. 11 depicts an example comparison of a measured performance of an acoustic transducer with a modeled performance of an acoustic transducer.

Responsive to forming the acoustic transducer, a response (e.g., performance) of the formed acoustic transducer may be measured, and the measured performance of the acoustic transducer may be compared to the modeled performance of the acoustic transducer, as shown in act 1022 of FIG. 10. FIG. 11 depicts an example comparison 1100 of a measured performance with a modeled performance.

The method 1000 may include iterating any of the acts of method 1000 to match modeled performance to measured performance as shown in act 1024 of FIG. 10. For example, act 1024 may include iteratively modeling materials and structures (e.g., apertures, bonding layers, etc.) of one or more elements of the acoustic transducer to match measured performance.

Additionally, any of the acts of method 400 of FIG. 4 may be utilized within method 1000 of FIG. 10. Furthermore, one or more of the piezoelectric ceramic material or the backing may be designed and formed via any of the actions of FIG. 10 as well.

Figure 12:
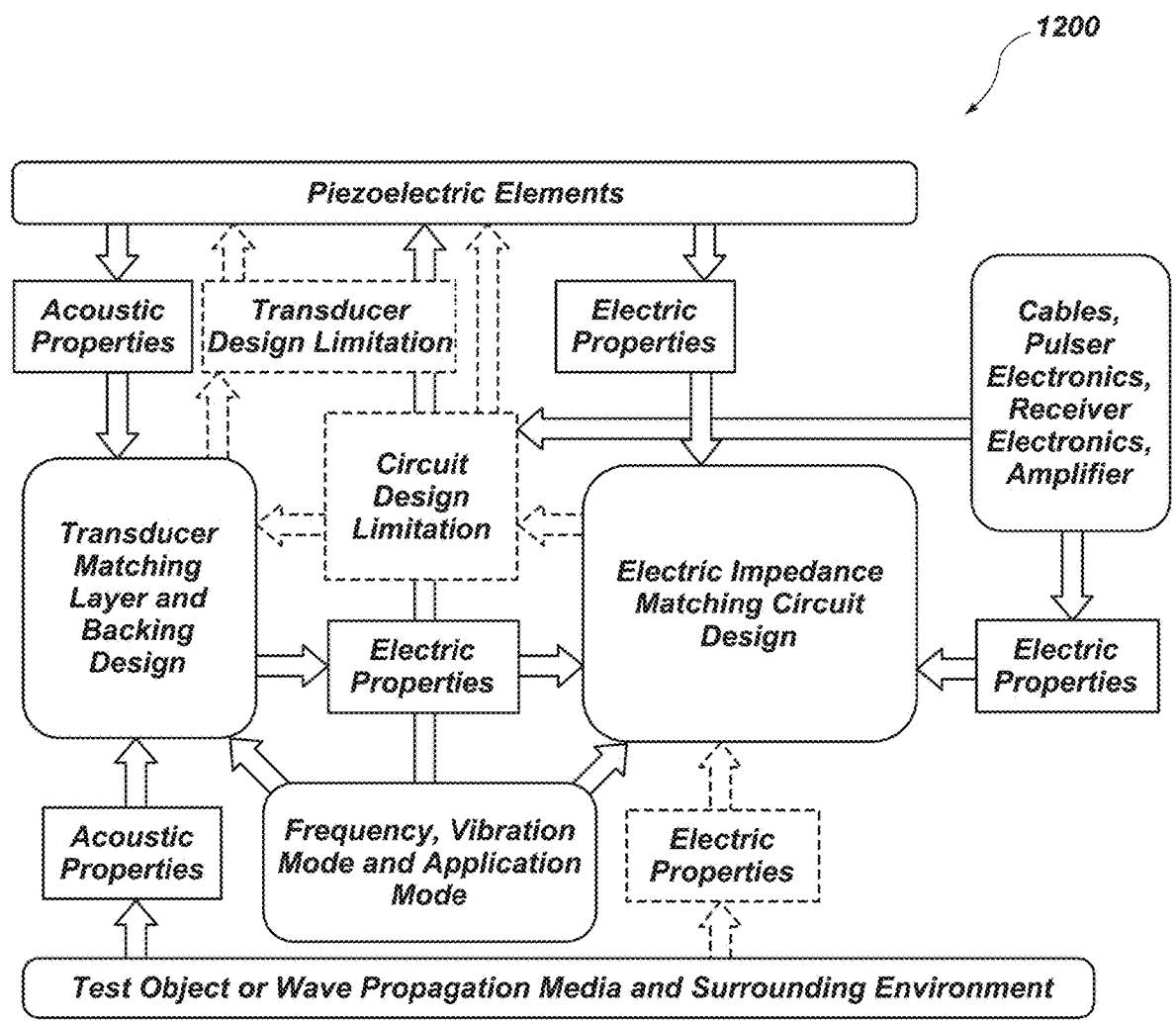
FIG. 12 depicts a schematic flowchart of a method for designing an acoustic transducer according to one or more embodiments of the present disclosure.

FIG. 12 depicts a schematic flowchart of a method 1200 for designing an acoustic transducer according to one or more embodiments of the present disclosure. For example, the method 1200 may account for electrical systems and properties in designing an acoustic transducer. As a non-limiting example, the method 1200 may include designing an acoustic transducer according to any of the manners described in *A Review of Acoustic Impedance Matching Techniques for Piezoelectric Sensors and Transducers, Sensors*, Vivek T. Rathod, Sensors 20 (14): 4051, (21 Jul. 2020), the disclosure of which is incorporated in its entirety by reference herein. Furthermore, embodiments of the present disclosure may include designing an acoustic transducer utilizing one or more acts of the method 1200 shown in FIG. 12 and forming the acoustic transducer via one or more of the manners described above in regard to FIGS. 2, 4, and 6.

The embodiments of the disclosure described above and illustrated in the accompanying drawings do not limit the scope of the disclosure, which is encompassed by the scope of the appended claims and their legal equivalents. Any equivalent embodiments are within the scope of this disclosure. Indeed, various modifications of the disclosure, in addition to those shown and described herein, such as alternative useful combinations of the elements described, will become apparent to those skilled in the art from the description. Such modifications and embodiments also fall within the scope of the appended claims and equivalents.

What is claimed is:

1. A method of designing at least one element of an acoustic transducer, the method comprising:
   receiving two or more required operating parameters of the at least one element of the acoustic transducer for an application, the at least one element chosen from an impedance matching layer, a ceramic crystal, and a backing material, and the two or more required operating parameters chosen from two or more of excitation levels, attenuation of back reflection, phase linearity, sensitivity, pulse-length, and pulse width;
   iteratively modeling and simulating performance of one or more materials relative to the two or more required operating parameters to utilize within the at least one element of the acoustic transducer;
   iteratively modeling and simulating performance of one or more structures relative to the two or more required operating parameters to utilize within the at least one element of the acoustic transducer; and
   identifying at least one material and at least one structure that exhibit predicted performance that at least substantially achieves the two or more required operating parameters of the at least one element of the acoustic transducer for the application, the at least one material comprises one or more of a high temperature resin, polyetherimide, a nickel-chromium alloy, a stainless steel, nickel, silicon bronze, MONEL, or any alloys of foregoing materials.

2. The method of claim 1, further comprising outputting a design of the at least one element of the acoustic transducer based at least partially on the identified at least one material and the identified at least one structure.

3. The method of claim 2, further comprising forming the at least one element of the acoustic transducer via one or more additive manufacturing processes.

4. The method of claim 3, wherein the one or more additive manufacturing processes comprises one or more of binder jetting, stereolithography (SLA), sol-gel or liquid dispense methods, inkjet 3D printing, direct metal deposition, micro-plasma powder deposition, direct laser sintering, selective laser sintering, electron beam melting, or electron beam freeform fabrication.

5. The method of claim 1, wherein identifying the at least one material comprises identifying each of a lead zirconium titanate and a polymer binder.

6. The method of claim 1, wherein iteratively modeling and simulating performance of the one or more materials and structures comprises utilizing one or more machine learning techniques to iteratively model and simulate the performance of the one or more materials and the one or more structures.

7. The method of claim 6, wherein the one or more machine learning techniques comprise one or more of quadratic regression analysis, logistic regression analysis, support vector machines, Gaussian process regression, ensemble models, decision tree learning, regression trees, boosted trees, gradient boosted trees, multilayer perceptron, one-vs-rest, Naïve Bayes, k-nearest neighbor, association rule learning, neural networks, deep learning, or pattern recognition.

8. The method of claim 1, wherein receiving the two or more required operating parameters comprises receiving requirements regarding a footprint requirement for the acoustic transducer.

9. The method of claim 1, wherein the at least one element comprises at least a backing layer of the acoustic transducer.

10. The method of claim 1, wherein the at least one element comprises at least a matching layer of the acoustic transducer.

11. The method of claim 1, wherein the at least one element comprises at least a piezoelectric ceramic crystal of the acoustic transducer.

12. A method of forming a plurality of elements of an acoustic transducer, the method comprising:
    receiving a three-dimensional model design of the plurality of elements of the acoustic transducer;
    forming the plurality of elements of the acoustic transducer via one or more additive manufacturing processes; and
    forming at least one element of the plurality of elements of the acoustic transducer with one or more of a high temperature resin, a nickel-chromium alloy, a stainless steel, nickel, silicon bronze, MONEL, or any alloys of foregoing materials.

13. The method of claim 12, wherein the one or more additive manufacturing processes comprise one or more of binder jetting, stereolithography (SLA), sol-gel or liquid dispense methods, inkjet 3D printing, direct metal deposition, micro-plasma powder deposition, direct laser sintering, selective laser sintering, electron beam melting, or electron beam freeform fabrication.

14. The method of claim 12, wherein forming the plurality of elements of the acoustic transducer via the one or more additive manufacturing processes comprises forming each of a piezoelectric ceramic crystal, a matching layer, and a backing layer via the one or more additive manufacturing processes.

15. The method of claim 12, wherein forming the plurality of elements of the acoustic transducer via the one or more additive manufacturing processes comprises forming only one of a piezoelectric ceramic crystal, a matching layer, and a backing layer via the one or more additive manufacturing processes.

16. The method of claim 12, wherein forming the plurality of elements of the acoustic transducer via the one or more additive manufacturing processes comprises:
    forming a first element of the acoustic transducer via a first additive manufacturing process;
    forming a second element of the acoustic transducer via a second additive manufacturing process; and
    assembling the first and second elements of the acoustic transducer.

17. The method of claim 12, wherein forming the plurality of elements of the acoustic transducer via the one or more additive manufacturing processes comprises forming at least one element of the plurality of elements with a nickel chromium alloy.

18. The method of claim 12, wherein forming the plurality of elements of the acoustic transducer via the one or more additive manufacturing processes comprises forming at least one element of the plurality of elements with each of a lead zirconium titanate and a polymer binder.

19. A method of forming an acoustic transducer, the method comprising:
    receiving two or more required operating parameters of each of a piezoelectric ceramic crystal, a matching layer, and a backing layer of the acoustic transducer for an application, the one or more required operating parameters chosen from excitation levels, attenuation of back reflection, phase linearity, sensitivity, pulse-length, and pulse width;
    iteratively modeling and simulating performance of one or more materials relative to the two or more required operating parameters to utilize within the piezoelectric ceramic crystal, the matching layer, and the backing layer of the acoustic transducer;
    iteratively modeling and simulating performance of one or more structures relative to the two or more required operating parameters to utilize within the piezoelectric ceramic crystal, the matching layer, and the backing layer of the acoustic transducer;
    identifying at least one material and at least one structure that exhibit predicted performance that at least substantially achieves the two or more required operating parameters of each of the piezoelectric ceramic crystal, the matching layer, and the backing layer of the acoustic transducer for the application, the at least one material comprises one or more of a high temperature resin, polyetherimide, a nickel-chromium alloy, a stainless steel, nickel, silicon bronze, MONEL, or any alloys of foregoing materials;
    outputting a design of each of the piezoelectric ceramic crystal, the matching layer, and the backing layer of the acoustic transducer based at least partially on the identified at least one material and the identified at least one structure of each of the piezoelectric ceramic crystal, the matching layer, and the backing layer of the acoustic transducer; and
    forming each of the piezoelectric ceramic crystal, the matching layer, and the backing layer of the acoustic transducer via one or more additive manufacturing processes.

* * * * *